United States Patent [19]

Marsh

[11] Patent Number: 5,685,291

[45] Date of Patent: Nov. 11, 1997

[54] NEBULIZER ADAPTER SYSTEM FOR PREMATURE BABIES

[76] Inventor: Jean Ann Marsh, 7721 S. Yale #309, Tulsa, Okla. 74136

[21] Appl. No.: 751,995

[22] Filed: Nov. 15, 1996

[51] Int. Cl.[6] ................................................. A61M 11/00
[52] U.S. Cl. ............................................................ 128/200.15
[58] Field of Search ............................ 128/200.11, 200.12, 128/200.13, 200.14, 200.15, 203.12, 203.15, 203.23, 203.24

[56] References Cited

U.S. PATENT DOCUMENTS

| | | | |
|---|---|---|---|
| 1,395,948 | 11/1921 | Drager | 128/206.29 |
| 1,592,345 | 7/1926 | Drager | 128/207.17 |
| 2,693,182 | 11/1954 | Phillips | 128/200.26 |
| 4,470,413 | 9/1984 | Warncke | 128/201.18 |
| 4,520,809 | 6/1985 | De Greef et al. | 128/200.24 |
| 4,896,666 | 1/1990 | Hinkle | 128/202.13 |
| 5,012,804 | 5/1991 | Foley et al. | 128/200.23 |
| 5,146,913 | 9/1992 | Khorsandian et al. | 128/200.26 |
| 5,318,523 | 6/1994 | Lu | 604/77 |
| 5,368,024 | 11/1994 | Jones | 128/207.17 |
| 5,375,593 | 12/1994 | Press | 128/207.18 |
| 5,462,050 | 10/1995 | Dahlstrand | 128/207.18 |
| 5,507,278 | 4/1996 | Karell | 128/200.23 |
| 5,512,047 | 4/1996 | Dvorak | 604/77 |

*Primary Examiner*—V. Millin
*Assistant Examiner*—Eric P. Raciti
*Attorney, Agent, or Firm*—Head Johnson & Kachigian

[57] ABSTRACT

A medication nebulizer adapter system for administering aerosol treatments for newborn and pediatric patients. The nebulizer adapter system of the invention includes an adapter for positioning in the mouth of the infant. The adapter serves to depress the tongue of the infant and to deliver nebulized medication to the rearward area of the infant's throat, where the medication may be subsequently inhaled into the lungs of the infant. By directing the medication to the infant's throat, as opposed to through the nose of the patient, the filtering effect of the nasal passageways may be avoided, thereby more efficiently delivering nebulized medication to the lungs of the patient.

20 Claims, 2 Drawing Sheets

NEBULIZER ADAPTER SYSTEM FOR PREMATURE BABIES

BACKGROUND OF THE INVENTION

The present invention relates to a method and apparatus for delivering nebulized medication to a patient. More particularly, this invention relates to a method and apparatus for delivering nebulized medication to a premature infant suffering from bronchopulmonary dysplasia (BPD). The nebulized medication is delivered to the back of the throat of the infant where it can be inhaled into the infant's lungs.

Several forms of chronic lung disease can be distinguished in a neonate, and each of these illnesses implies a long-term dependence on supplemental oxygen. In addition, these conditions frequently are characterized by elevated blood carbon dioxide levels resulting from an inadequate surface area for gas exchange in the lungs. In a very low birth weight infant (less than 1000 grams), most common among these problems is chronic pulmonary insufficiency of prematurity (CPIP). Herein, the alveoli are forced to mature under the constant stress of the oxygen content of room air, which is approximately six times greater than that of the developing air sacs when the lungs are fluid-filled in utero. Lung growth is therefore delayed and leads to a long-term oxygen dependency. Gradually, as the nutritional status of the baby improves, the alveoli grow and most children are weaned from oxygen within the first six months of life. BPD is a chronic lung disorder in infants who have been treated for respiratory distress with intermittent mandatory ventilation. BPD is a variation of chronic lung disease that emanates from life-saving, therapeutic maneuvers in the treatment of children with acute respiratory illnesses.

Combinations of the supplemental oxygen required, (especially in amounts of greater than 40%), positive pressure, and the trauma of mechanical ventilation inevitably lead to changes in an infant's airways, which become thickened with increased mucous production. However, assuming no major intervening illness, the majority of survivors acquire relatively normal lung function by the time they reach the elementary school years. The oxygen and pressure to the lungs that help save a baby's life during the critical phase of BPD can paradoxically also delay recovery. Some babies on a respirator for a week or more develop BPD resulting in damage to the lungs and bronchioles from high oxygen doses or high respirator pressures. The damaged tissue dies and forms scars that impede the passage of air in and out of the lungs and obstruct the exchange of oxygen and carbon dioxide between the lungs and the bloodstream.

Unlike an adult with lung disease, a baby with BPD can grow healthy new lung tissue. And while scarring in the bronchioles is permanent, the bronchioles eventually grow and expand to the point where the scar tissue no longer hampers air flow to and from the lungs. However, until the lungs have healed sufficiently, the baby continues to be dependent on the respirator and/or supplemental oxygen—a dependency that may take weeks or months to resolve.

A baby with BPD often suffers from excessive fluid accumulation in his lungs and other body tissues. He may be treated with an aerosolized bronchodilator such as Albuteral and a diuretic such as furosemide (Lasix) to help him excrete these fluids. Additionally, infants suffering from BPD often receive aerosol treatments for their congestion and wheezing. Such treatments are often frequently administered, e.g. every two hours. Typically, newborn and pediatric aerosols have been administered via a reservoir to the nares. This procedure is known as "flow by". Newborns and babies, particularly premature babies, are considered to be obligatory nose breathers, due to the position of an infant's tongue. The positioning of the tongue prevents newborns and babies from easily breathing through their mouths. Consequently, the administering of medication through aerosol perfusion is inefficient due to the particle size of the nebulized medications being inhaled through the nose of the infant. Air inhaled through the nose is naturally filtered, thereby reducing the amount of medication which reaches the lungs of the patient. Additionally, the effectiveness of administering nebulized medication via a reservoir to the nares is limited by cooperation from the patient.

Previously, nebulized medication was administered by using an apparatus to blow an aerosol stream in the baby's face so that the medication could be inhaled by the infant. An example of such a device is a twin jet unit that is a non-pressurized aerosol nebulizer.

Examples of nebulizers having a mouthpiece include U.S. Pat. No. 1,395,948 for "Helmet and Mask for Use With Respiratory Apparatus" and U.S. Pat. No. 1,592,345 for "Mouthpiece for a Respiratory Apparatus", both issued to Draeger. Other examples include U.S. Pat. No. 2,693,182 to Phillips for an "Oro-Tracheal Tube Positioner and Retainer", and U.S. Pat. No. 5,146,913 to Khorsandian et al for a "Holder and Lock for Oro-Intubation".

None of the previous devices allow a nebulized medication to be delivered to the back of the throat of an infant, thereby enabling the nebulized medication to be inhaled into the lungs of the infant without passing through the infant's nasal passageways.

BRIEF SUMMARY OF THE INVENTION

To avoid the difficulties associated with treating infants who have an aversion to aerosol treatments, nebulized medication may be administered through an open-ended nipple or adapter. The open-ended nipple or adapter depresses the tongue of the infant. Therefore, by using such a device, the nebulized medication is able to bypass the tongue and be delivered to the back of an infant's throat. The nebulized medication may then be inhaled by the infant.

It is therefore an object of the invention to provide a method and apparatus to deliver medication to the rearward area of the throat of an infant so that the medication can be inhaled into the lungs.

It is a further object of the invention to deliver nebulized medication to an infant wherein the medication does not pass through the nose of the infant. By directing the medication such that the medication is inhaled through the mouth of the infant, none of the medication is subjected to the filtering action of the nasal passageways. The present invention contemplates affixing an open-ended nipple or adapter to a nebulizer. The open-ended nipple or adapter, when placed in an infant's mouth, depresses the tongue of the infant. The depressing of an infant's tongue enables medication to be administered to the rear of the throat of the infant, thereby allowing the infant to inhale the nebulized medication directly into his or her lungs.

A typical nebulizer comprises a medication reservoir, wherein liquid medication is stored. The reservoir has a means for injecting pressurized air into the medication, thereby nebulizing the medication. The nebulized medication travels through a passageway into a horizontal conduit. Currently, the conduit is fixed with a dispersing device which is waved in front of a baby's face so that the infant can inhale the nebulized medication through the infant's nostrils.

The improved design of the Applicant's invention comprises replacement of a dispersing attachment with an open-ended nipple or adapter. By utilizing the adapter, which is placed in the baby's mouth, the medication can be administered to the lungs of the infant without being filtered by the nasal passageways of the infant. The result is a more efficient means to administer medication to an infant's lungs.

The Nebulizer Adapter System can also be used with metered dose inhalers (MDI). Without such an adapter, difficulties are typically experienced when attempting to use an MDI with infants or small children.

DETAILED DESCRIPTION OF THE INVENTION

Figure 1:
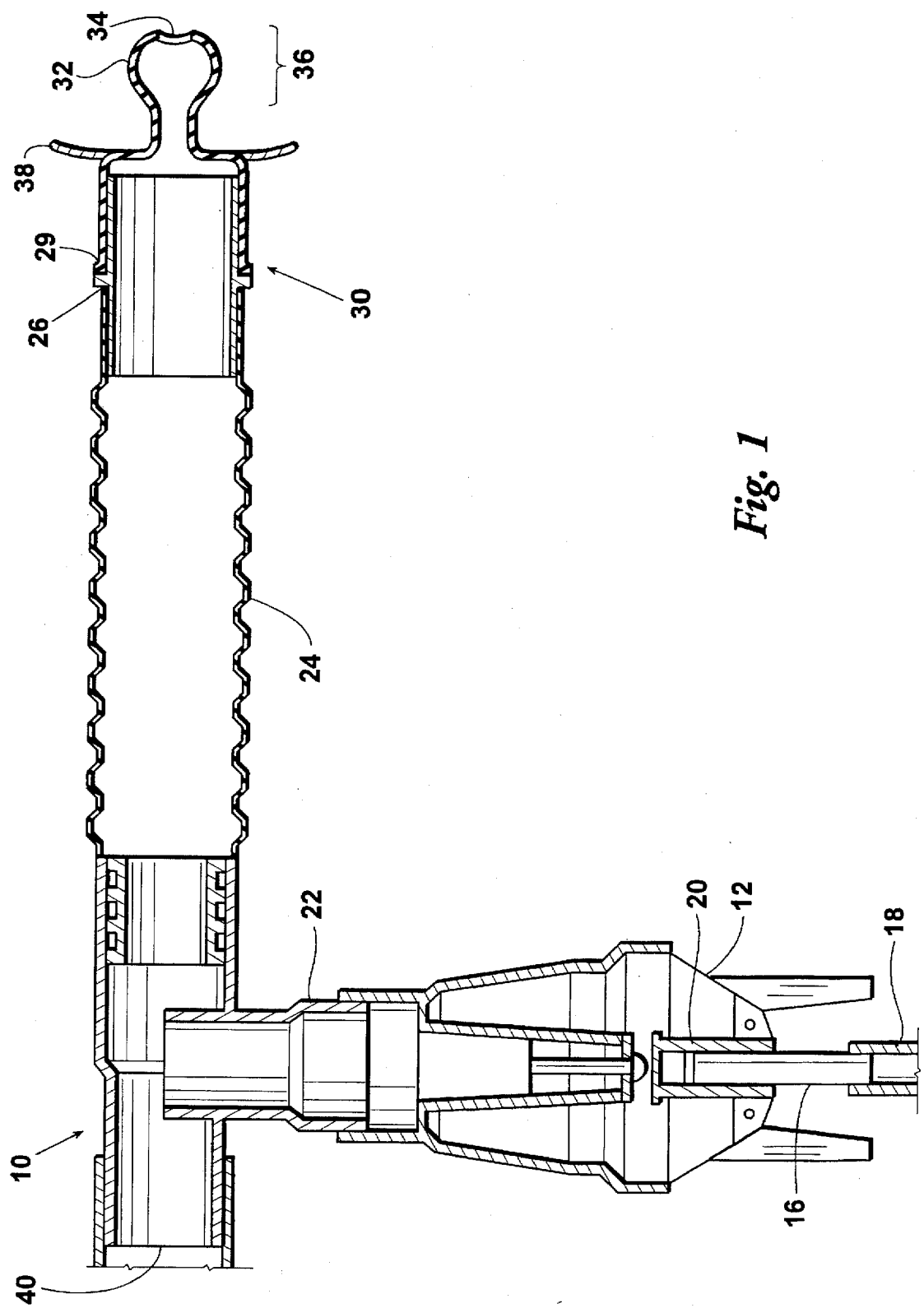
FIG. 1 shows an elevational view of the improved nebulizer adapter system.

Referring to FIG. 1, shown is a typical sidestream nebulizer designated generally 10. The typical sidestream nebulizer is comprised of reservoir 12 for containing medication 14. Pressurized air orifice 16 is provided on reservoir 12 to admit a stream of pressurized air into reservoir 12 via tubing 18. Pressurized air is exited through jet 20 for the purpose of nebulizing medication 14. Nebulized medication 14 travels up passageway 22 where it then migrates down conduit 24 to dispensing end 26 of conduit 24. Affixed to dispensing end 26 is connecting end 28 of the adapter, designated generally 30. Adapter 30 is comprised of terminal end 32 having orifice 34 located therein. In the preferred embodiment, orifice 34 is approximately 10 mm or less in diameter. In the preferred embodiment, terminal end 32 comprises a semi-spherical area 36 so that adapter 30 is approximately the shape of a typical pacifier. A good seal with the patient's face is assured by utilizing flange 38, which is preferably affixed to adaptor 30. Flange 38 additionally safeguards against adapter 30 being swallowed by the patient. Any nebulized medication not passing through adapter 30 may be exhausted through exhaust orifice 40, located on nebulizer 10; or, other types of standard exhalation valve assemblies may be used and placed in closer proximity to adapter 26. Additionally, in the preferred embodiment, adapter 30 is constructed of a pliable, soft material. In another embodiment, adapter 30 is comprised of a typical pacifier having orifice 34 fashioned in a terminal end thereof. Although a typical sidestream nebulizer is discussed herein, it shall be understood that any number of standard pneumatic nebulizers may be used with this Nebulizer Adapter System.

In practice, nebulizer 10 is used to nebulize medication 14 by receiving pressurized air through pressurized air orifice 16 and dispensing it into medication 14 by means of air jet 20. Nebulized medication travels up passageway 22, where it then migrates down conduit 24. The nebulized medication is then transferred to the patient's mouth via adapter 30. Adapter 30, affixed to dispensing end 26 of conduit 24, is placed into an infant's mouth. Adapter 30 is typically well-received by an infant since adapter 30 is preferably comparable in shape to a typical pacifier. The nebulized medication is then free to exit through orifice 34 into the rearward area of the throat of an infant. Adapter 30 serves to depress the tongue of the infant, thereby removing an obstruction to the path of the medication such that the medication can freely travel to the rearward area of the infant's throat, where the nebulized medication may be inhaled into the lungs of the infant.

Figure 2:
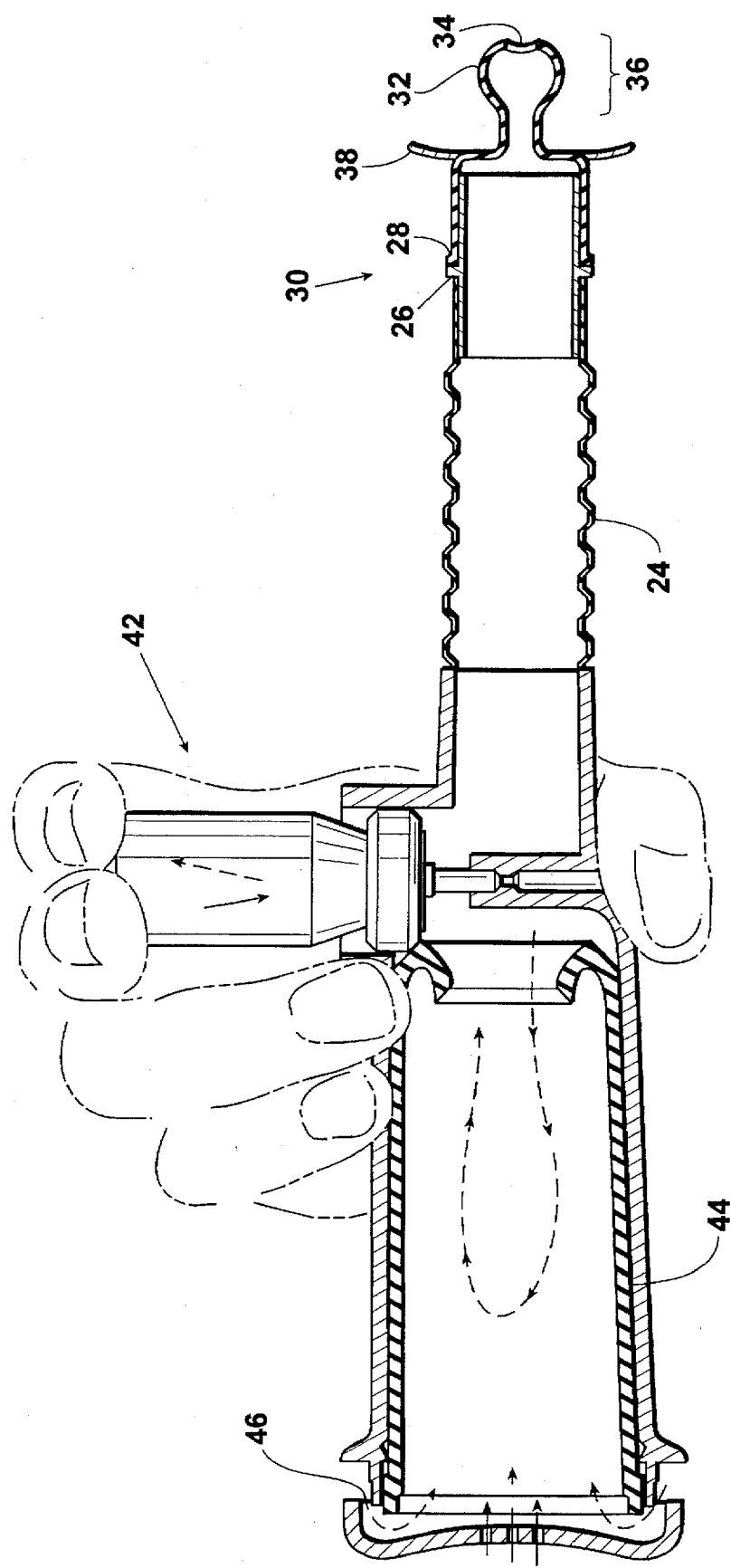
FIG. 2 shows an enlarged view of the adapter.

Referring now to FIG. 2, shown is the Applicant's Nebulizer Adapter System in use with a metered dose inhaler (MDI), designated generally 42. MDI 42 is shown in use with spacer 44. Spacer 44 is provided with air inlet 46. Affixed to MDI 42 is conduit 24, with the accompanying elements of the Applicant's Nebulizer Adapter System which are present in the embodiment of FIG. 1. By utilizing Applicant's Nebulizer Adaptor System, MDI 42 may be easily utilized with infants and small children.

In practice, nebulizer adaptor 30 is affixed to typical MDI 42 by means of conduit 24. By utilizing adaptor 30, the nebulized medication from MDI 42 is delivered to the rearward area of the throat of an infant. When MDI 42 is depressed nebulized medication is delivered into spacer 44. Nebulized medication then migrates up conduit 24, where it is then transferred to the patient's mouth via adapter 30. Adapter 30, affixed to dispensing end 26 of conduit 24 is placed into an infant's mouth. Adaptor 30 is typically well-received by an infant since adaptor 30 is preferably comparable in shape to atypical pacifier. The nebulized medication is then free to exit through orifice 34 into the rearward area of the throat of an infant. Adaptor 30 serves to depress the tongue of the infant, thereby removing an obstruction to the path of the medication such that the medication can freely travel to the rearward area of the infant's throat, where the nebulized medication may be inhaled into the lungs of the infant. By utilizing adapter 30, nebulized medication may be administered to an infant or child via an MDI without subjecting an infant to the unpleasant and startling sensation of having the nebulized medication burst directly out of MDI 42 and into the infant's or child's mouth.

Whereas the present invention has been described in relation to the drawings attached hereto, it should be understood that any number of standard pneumatic nebulizers, ultrasonic nebulizers, or MDI systems having applications for premature babies, infants, and small children may be used with this Nebulizer Adapter System, and that other and further modifications apart from those shown or suggested herein may be made within the spirit and scope of this invention.

What is claimed is:

1. A nebulizer system for use with infants and small children, said nebulizer system comprising:

a medication nebulizing means;

a conduit for transferring nebulized medication to a dispensing end; and said dispensing end having an adapter for insertion into a baby's mouth for transferring said nebulized medication to a rearward area of an infant's throat for subsequent inhalation.

2. A nebulizer system according to claim 1 wherein said nebulizing means comprises a reservoir for containing medication and a pressurized air inlet to deliver air into said reservoir for nebulizing the medication.

3. A nebulizer system according to claim 1 wherein said nebulizing means is a metered dose inhaler.

4. A nebulizer system according to claim 1 wherein said adapter depresses an infant's tongue.

5. A nebulizer system according to claim 1 wherein said adapter has a connecting end and a terminal end, said adaptor defining an orifice in said terminal end.

6. A nebulizer system according to claim 5 wherein said adapter terminal end is semi-spherical.

7. A nebulizer system according to claim 5 wherein said orifice is approximately 10 mm in diameter.

8. A nebulizer according to claim 5, wherein said orifice is less than 10 mm in diameter.

9. A nebulizer system according to claim 5 wherein said adapter is constructed of a pliable soft material.

10. A nebulizer system according to claim 1 wherein said adapter is a typical pacifier having an orifice in a terminal end thereof.

11. A nebulizer system according to claim 10 wherein said orifice is approximately 10 mm in diameter.

12. A nebulizer according to claim 10, wherein said orifice is less than 10 mm in diameter.

13. A method of delivering nebulized medication to a patient, said method comprising:

nebulizing medication;

transferring said nebulized medication to the patient's mouth via a conduit; and bypassing the patient's tongue by transferring said nebulized medication to a rearward area of the patient's mouth by channeling said nebulized medication through an adapter having an orifice.

14. A method of delivering nebulized medication to a patient according to claim 13, wherein said step of nebulizing medication comprises admitting a stream of pressurized air into a reservoir containing said medication.

15. A method of delivering nebulized medication to a patient according to claim 13, wherein said step of nebulizing medication comprises delivering medication via a metered dose inhaler.

16. A method of delivering nebulized medication according to claim 13, wherein said adapter has a terminal end, said terminal end having said orifice positioned thereon.

17. A method of delivering nebulized medication according to claim 16 wherein said adapter is approximately the shape of a pacifier.

18. A method of delivering nebulized medication according to claim 16 wherein said exit orifice is approximately 10 mm in diameter.

19. A method of delivering nebulized medication according to claim 16, wherein said exit orifice is greater than 10 mm in diameter.

20. A method of delivering nebulized medication according to claim 16 wherein said adapter is constructed of a pliable soft material.

* * * * *